United States Patent [19]

Braun

[11] Patent Number: 4,923,479

[45] Date of Patent: May 8, 1990

[54] COMPOSITION AND PROCESS FOR THE OXIDATIVE DYEING OF HAIR WITH 3-(2',2',2'-TRIFLUOROETHYL)AMINO-PHENOL DERIVATIVES

[75] Inventor: Hans-Jürgen Braun, Albligen, Switzerland

[73] Assignee: Wella Aktiengesellschaft, Darmstadt, Fed. Rep. of Germany

[21] Appl. No.: 221,793

[22] PCT Filed: Nov. 9, 1987

[86] PCT No.: PCT/EP87/00692

§ 371 Date: Aug. 4, 1988

§ 102(e) Date: Aug. 4, 1988

[87] PCT Pub. No.: WO88/04166

PCT Pub. Date: Jun. 16, 1988

[30] Foreign Application Priority Data

Dec. 4, 1986 [DE] Fed. Rep. of Germany ....... 3641630

[51] Int. Cl.$^5$ .......................... A61K 7/13; C07C 87/60
[52] U.S. Cl. ............................. 8/412; 8/407; 8/408; 8/421; 564/442; 564/443
[58] Field of Search ................... 8/407, 408, 412, 421; 564/442, 443

[56] References Cited

U.S. PATENT DOCUMENTS 3,811,831  5/1974  Bugaut et al. ........................... 8/412
4,395,262  7/1983  Konrad et al. ........................... 8/407
4,543,425  9/1985  Konrad et al. ....................... 564/442

FOREIGN PATENT DOCUMENTS 2951377  7/1981  Fed. Rep. of Germany .......... 8/421

3627398  2/1988  Fed. Rep. of Germany .......... 8/421

OTHER PUBLICATIONS

"Synthesis of Some Trifluoroethyl–Substituted Derivatives of Aniline", by Eugene R. Bissell and Rosalind W. Swansiger; *Journal of Fluorine Chemistry*, 12 (1978), pp. 293–305.

*Primary Examiner*—Paul Lieberman
*Assistant Examiner*—Linda A. Skaling
*Attorney, Agent, or Firm*—Michael J. Striker

[57] ABSTRACT

A composition and a process for the oxidative dyeing of hair based on a combination of developer substance and coupling substance, wherein there is used as the coupling substance a 3-(2',2',2'-trifluoroethyl)aminophenol derivative having the formula (I)

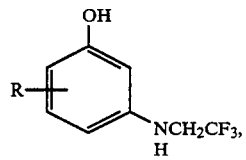

(I)

wherein the radical R represents an alkyl radical containing 1 to 4 carbon atoms, a mono- or polyhydroxyalkyl radical containing 1 to 4 carbon atoms and up to 3 hydroxyl groups, an alkoxy radical containing 1 to 4 carbons atoms, a mono- or polyhydroxy-alkoxy radical containing 1 to 4 carbons atoms and up; to 3 hydroxyl groups or a halogen atom or its physiologically compatible salt as well as novel 3'-(2',2',2'-trifluoroethyl)aminophenol derivatives.

14 Claims, No Drawings

COMPOSITION AND PROCESS FOR THE OXIDATIVE DYEING OF HAIR WITH 3-(2',2',2'-TRIFLUOROETHYL)AMINO-PHENOL DERIVATIVES

The present invention relates to an agent and a process for the oxidative dyeing of hair based on a combination of a developer substance and a coupling substance, wherein a 3-(2',2',2'-trifluorethyl)aminophenol derivative is used as well as to the novel 3,-(2',2',2'-trifluoroethyl)aminophenol derivatives per se.

In hair dyeing practice oxidation dyes have gained substantial importance. In oxidative dyeing the dyes are produced by oxidative coupling of developer substances and coupling substances in the hair shaft. This results in very intensive hair colorations with very good color fastness. Furthermore, different color shades can be produced by the combination of suitable developer substances and coupling substances.

Usually 1,4-diamino-benzene, 2,5-diamino toluene, 2,5-diamino-anisole and 4-aminophenol are used as developer substances. 2,5-diamino-benzyl alcohol and 2-(2',5'-diamino) phenyl-ethanol have also gained some importance.

These developer substances together with suitable coupling substances under the action of an oxidizing agent result in the hair colorations. Thus, for example, with the coupling substances resorcinol, 2-methyl resorcinol or 4-chloro resorcinol natural blond to light brown hair colors are obtained.

By combining the developer substances 1,4-diamino-benzene or 4-aminophenol with the coupling substances 5-amino-2-methylphenol and 1,3-diamino-benzene derivatives such as 2,4-diamino-anisole red hair colors can also be obtained.

Blue to blue-violet color shades are produced with 1,4-diamino-benzene or its derivatives, as for example, 2,5-diamino-toluene, or developer substance, requiring the use of 1,3-diamino-benzene derivatives as coupling substances.

Black hair colors can be obtained by combining the above-mentioned developer substances and coupling substances with further suitable coupling substances. However, the 1,3-diamino-benzene derivatives are considered to be toxicologically objectionable so there exists a need of a substitute for these substances in a hair dye.

Several attempts have been made to replace the 1,3-diamino-benzene derivatives by the 3-aminophenol derivatives, which are generaly regarded as being toxicologically more suitable. However, with the conventional coupling substances 3-aminophenol and 5-amino-2-methylphenol only red hair colors can be produced. Furthermore, with the coupling substance described in DE-OS 2,429,780, i.e., 5-amino-2-aminophenol, in combination with the developer substance 2,5-aminophenol a reddish violet shade is obtained. Therefore, the 5-amino-2-chlorophenol is not completely suitable as a substitute for 1,3-diamino-benzene.

Therefore, the present invention provides a hair dye based on a combination of a developer substance and a coupling substance, wherein the coupling substance is toxicologically more favorable than 1,3-diamino-benzene and has better dyeing properties than the conventional 3-aminophenol derivatives.

It has now been found that an agent for the oxidative dyeing of hair based on a combination of developer substance and coupling substance which contains as coupling substance a 3-(2',2',2'-trifluoro-ethyl)aminophenol derivative having the formula I

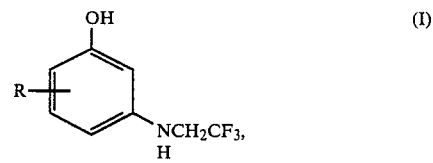

wherein the radical R represents an alkyl radical containing 1 to 4 carbon atoms, a mono- or polyhydroxyalkyl radical containing 1 to 4 carbon atoms and up to 3 hydroxyl groups, an alkoxy radical containing 1 to 4 carbon atoms, a mono- or polyhydroxy alkoxy radical containing 1 to 4 carbon atoms and up to 3 hydroxyl groups or a halogen atom or its physiologically compatible salt, is excellent for this purpose.

The radical R in the formula (I) can be in an ortho, meta or para position relative to the (2',2',2'-trifluoroethyl) amino radical, the para position relative to the (2',2',2'-trifluoroethyl)radical being preferred. Chlorine is preferred as the halogen atom.

As physiologically compatible salt with inorganic or organic acids, for example, the chloride, the sulphate, the phosphate, the acetate, the propionate, the lactate and the citrate may be mentioned.

As compared with the conventional 3-aminophenol derivatives it has now surprisingly been found that, for example, with the coupling substance 2-chloro-5-(2',2',2'-trifluoroethyl)aminophenol in combination with the developer substances 1,4-diaminobenzene, 2,5-diaminotoluene, 2,5-diaminobenzyl alcohol or 2-(2',5'-diamino)phenol-ethanol pure blue colorations of the hair are obtained without a red component. The compound 2-chloro-5-(2',2',2'-trifluoroethyl)aminobenzene thus constitutes the first 3-aminophenol derivative having the dyeing properties of a typical blue coupling substance. In combination with the developer substance 4-aminophenol the 2-chloro-5-(2',2',2'-trifluoroethyl)aminophenol dyes the hair to a pure red.

The conventional coupling substance 5-amino-2-chlorophenol does not have this dyeing capacity. The combination of 5-amino-2-chlorophenol with 4-aminophenol as developer substance produces only a red-brown shade.

The coupling substance 2-chloro-5-(2',2',2'-trifluoroethyl)aminophenol thus has the favorable dyeing properties of a 1,3-diaminobenzene derivative and, in addition, it has the toxicological properties of the 3-aminophenol derivatives which are better than those of the 1,3-diaminobenzene derivatives. Therefore, it is possible to replace with advantage the toxicologically objectionable 1,3-diaminobenzene derivatives used in hair dyes heretofore.

The other coupling substances having the formula (I), i.e., 2-methyl-5-(2',2',2'-trifluoroethyl)aminophenol, 2-methyl-3-(2',2',2'-trifluoroethyl)aminophenol and 2-methoxy-5-(2',2',2'-trifluoroethyl)aminophenol dye the hair in combination with the developer substances 1,4-diamino-benzene, 2,5-diamino toluene, 2,5-diamino-benzyl alcohol or 2-(2',5'-diamino)phenolethanol in claret to red-violet shades and constitute an extension of the dyeing possibilities in the range of modern red shades.

The coupling substance having the formula (I) is to be contained in the hair dyes according to the present invention in an amount of approximately 0.01 to 4.0 percent by weight, preferably 0.02 to 2.0 percent by weight.

The coupling substance having the formula (I) is usually used in an approximately equimolar amount, relative to the developer substances used. Although it has been found that the equimolar amount is appropriate, it is not disadvantageous to apply the coupling substance in a certain excess or in an amount falling short of the equimolar amount. Furthermore, it is not required that the developer component and the coupling component are homogeneous products. On the contrary, both the developer component can be a mixture of conventional developer substances and the coupling component can be a mixture of the compound according to the present invention and conventional coupling substances.

Amongst the conventional developer substances primarily the following substances are suitable as a component of the hair dyes according to the present invention: 1,4-diamino-benzene, 2,5-diamino-toluene, 2,5-diamino-anisole, 4-aminophenol, 2,5-diamino-benzyl alcohol and 2-(2',5'-diamino)phenyl-ethanol. Of course, other developer substances, as for example, 3-methyl-4-amino-phenol or tetraamino-pyrimidine, can also be used.

Furthermore, conventional coupling substances can be additionally contained in the hair dyes, particularly resorcinol, 4-chloro resorcinol, 4,6-dichloro resorcinol, 2-methyl resorcinol, 2-amino-4-(2'-hydroxyethyl)amino anisole, 1,5-dihydroxy tetralin, 3-amino-2-methyl-phenol, 2,4-diamino-anisole, 2,4-diamino-benzyl alcohol, 5-amino-2-methylphenol, 2,4-diamino-phenetole, 1,3-diamino-benzene, 1-naphthol, 4-hydroxy indole, 5-hydroxy-benzodioxole-(1,3), 5-amino-benzodioxole-(1,3), 5-(2'-hydroxyethyl)amino benzodioxole (1,3), 2,4dihydroxy-anisole and 2,4-dihydroxy-phenoxy-ethanol, either alone or in mixture with each other.

These oxidation dyes which are known and used in hair dyeing are also described in the book by E. Sagarin, "Cosmetics, Science and Technology", Interscience Publishers Inc., New York (1957), Page 503 ff. as well as in the book by H. Janistyn "Handbuch der Kosmetika und Riechstoffe" (1973), Page 338 ff.

The total amount of the combination of developer substance and coupling substance contained in the claimed hair dyes should be approximately 0.1 to 6.0 percent by weight, preferably 0.5 to 3.0 percent by weight.

In order to attain specific shades, conventional direct dyes, for example, triphenyl methane dyes such as Diamond Fuchsine (C.I. 42510) and Leather Ruby (C.I. 42 520), aromatic nitro dyes, as for example, 2-(2'-hydroxy-etyl)amino-4,6-dinitro-phenol, 4-(2'-hydroxyethyl)amino-2-nitro-aniline and 2-amino-4-nitrophenol, azo dyes, as for example, Acid Brown 4 (C.I. 14 805) and Acid Blue 135 (C.I. 13 385), anthraquinone dyes, as for example, Disperse Violet 4 (C.I. 61 105), Disperse Blue 1 (C.I. 64 500), Disperse Red 15 (C.I. 60 710), Disperse Violet 1 (C.I. 61 100) as well as 1,4,5,8-tetraamino-anthraquinone and 1,4-diamino-anthraquinone can also be contained in the hair dyes.

Further suitable direct hair dyes are described, for example, in the book by J. C. Johnson, 37 Hair Dyes", Noyes Data Corp., Park Ridge, USA (1973), Page 3 to 91 and 113 to 139 (ISBN: 0-8155-0477-2).

Furthermore, the hair dye can also contain self-coupling color prestages, as for example, 2-amino-5-methyl-phenol, 2-amino-6-methylphenol and 2-amino-5-ethoxy-phenol.

The total amount of the direct dyes and of the self-coupling color prestages should be approximately 0.1 to 3.0 percent by weight.

In addition, the hair dye can also contain further additives which are customary for these kind of agents, for example, antioxidants such as ascorbic acid or sodium sulphate, perfume oils, complexing agents, wetting agents, emulsifiers, thickeners, care agents, etc. The preparation can be in the form of a solution, particularly an aqueous or aqueous-alcoholic solution. However, the particularly preferred forms of preparation are a cream, a gel or an emulsion.

Its composition is a mixture of the dye components with the conventional additives used for these preparations.

Conventional additives in solutions, creams, emulsions or gels are, for example, solvents such as water, lower aliphatic alcohols, for example, ethanol, propanol or isopropanol, as well as polyhydric alcohols such as ethylene glycol, 1,2-propylene glycol and glycerol, and also wetting agents or emulsifiers from the classes of the anionic, cationic, amphoteric or non-ionogenic surfactants, as for example, fatty alcohol sulphates, oxethylated fatty alcohol sulphates, fatty acid taurides, alkyl sulphonates, alkyl-benzenes sulphonates, alkyl-trimethyl ammonium salts, alkyl betaines, oxethylated fatty alcohols, oxethylated nonyl phenols, fatty acid alkanol amides, oxethylated fatty esters, and also thickeners, as for example, higher fatty alcohols, starch, polyacrylic acid, cellulose derivatives, alginates, vaseline, paraffin oil and fatty acids and also care agents, as for example, lanolin derivatives, cholesterol, pantothenic acid and betaine.

The above-mentioned additives are applied in the amounts customary for these purposes, for example, the wetting agents and emulsifiers in concentrations of approximately 0.5 to 30 percent by weight, while the thickeners can be contained in the preparations in an amount of approximately 0.1 to 25 percent by weight and the care agents in an amount of approximately 0.1 to 5 percent by weight.

Depending on the composition the hair dye, according to the present invention, can react weakly, neutral or alkaline. In particular, it has a pH value in the alkaline range of between 8.0 and 11.5, the adjustment being carried out preferably with ammonia. However, organic amines, for example, monocethanol amine or triethanol amine or even inorganic bases such as sodium hydroxide and potassium hydroxide can also be used.

In the process according to the present invention for the oxidative dyeing of hair the above-described hair dye is mixed with an oxidizing agent immediately prior to its use and an amount adequate for the treatment of the hair, usually about 50 to 150 g of this mixture (depending on the fullness of the hair) are applied to the hair. Primarily hydrogen peroxide, for example, as a 6 percent aqueous solution, and its addition products to urea, melamine or sodium borate in the form of a 3 to 12 percent aqueous solution are suitable as oxidizing agents for the development of the hair dye. On using a 6 percent hydrogen peroxide solution as oxidizing agent the weight ratio of hair dye to oxidizing agent is 5:1 to 1:2, but preferably 1:1. Larger amounts of oxidizing agent are used primarily at higher dye concentrations in the hair dye or when a more intense bleaching of the hair is intended at the same time. The mixture is allowed to act on the hair at 15° to 50° C. for approximately 10 to 45 minutes, preferably for 30 minutes, whereupon the hair is rinsed with water and dried. When required, the rinsing is followed by washing with a shampoo and finally by rerinsing with a weak physiologically compatible organic acid, as for example, citric acid or tartaric acid, and the hair is then dried.

The hair colorations attainable with the 3-(2',2',2'-trifluoroethyl)aminophenol derivative having the formula (I) as coupling substance have a good light fastness, permanent wave fastness, fastness to acid and rubbing fastness. The shades are also stable against the action of light, chemical agents and rubbing.

The present invention also provides a 3-(2',2',2'-fluoroethyl)aminophenol derivative having the formula (II)

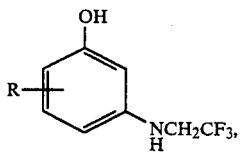

wherein the radical R represents an alkyl radical containing 1 to 4 carbon atoms, a mono- or polyhydroxyalkyl radical containing 1 to 4 carbon atoms and up to 3 hydroxyl groups, an alkoxy radical containing 1 to 4 carbon atoms, a mono- or polyhydroxy-alkoxy radical containing 1 to 4 carbon atoms and up to 3 hydroxyl groups or a halogen atom with the proviso that if the radical R is in the para position relative to the hydroxyl group, R does not represent alkyl.

Examples of compounds having the formula (I) are 2-methyl-3-(2'2'2'-trifluoroethyl)aminophenol, 2-methyl-5-(2',2',2'-trifluoroethyl)aminophenol, 2-chloro-5-(2',2',2'-trifluoroethyl)aminophenol, 2-methoxy-5-(2',2',2'-trifluoroethyl)aminophenol and 3-methyl-5-(2',2',2'-trifluoroethyl)aminophenol.

The production of the known compound 4-methyl-3-(2',2',2'-trifluoroethyl)aminophenol is described in the literature (see E. R. Bissel et al., Journal of Fluorine Chemistry 12, 293 (1978)).

The components having the formula (II) were produced by reducing a correspondingly substituted trifluoro acetic acid amide derivative with sodium boron hydride in the presence of a Lewis acid.

In the present case the reduction is carried out in a cyclic ether, for example, tetrahydrofuran or dioxane, as solvent.

For example, boron-trifluoride etherate, aluminium trichloride or titanium tetrachloride are suitable as Lewis acid.

The examples hereafter are intended for explaining the present invention in greater detail without restricting it thereto.

EXAMPLES OF PRODUCTION

Example 1: Production of 2-methyl-5-(2',2',2'-trifluoroethyl) aminophenol

Stage 1: N-(3-hydroxy-4-methyl) phenyl-2',2',2'-trifluoroacetamide

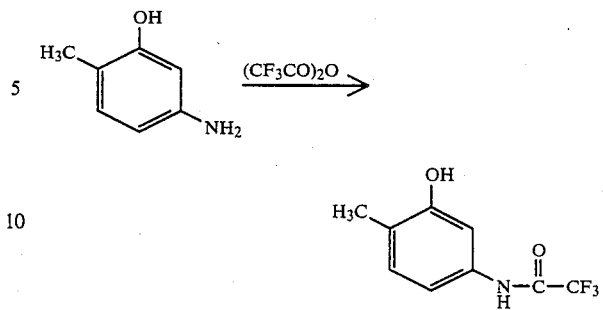

6.16 g (50 mmoles) of 5-amino-2-methylphenol are dissolved in 100 ml of diethyl ether, whereupon 10.4 ml (75 mmoles), 15.7 g) of trifluoroacetic acid anhydride are added dropwise at room temperature. As soon as the exothermic reaction is completed the diethyl ether is distilled off in a rotation evaporator. The crude product obtained is recrystallized in a mixture of ethanol and water (1:1), 8.0 g, (i.e., 73% of the theoretical yield) of a brown powder having a melting point of 130° to 133° C. are obtained

| CHN Analysis: | % C | % H | % N |
|---|---|---|---|
| $C_9H_8F_3NO_2$ computed: | 49.32 | 3.68 | 6.39 |
| obtained: | 49.65 | 3.78 | 6.35 |

Stage 2: 2-methyl-5-(2',2',2'-trifluoroethyl)aminophenol

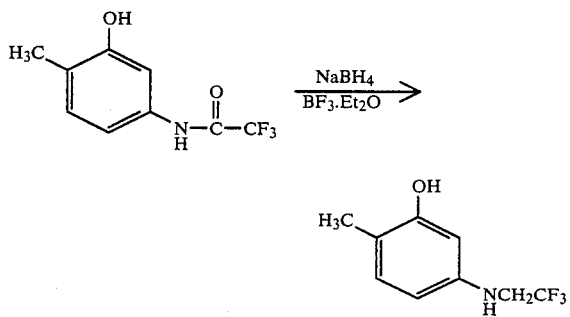

2,2 g (10 mmoles) of product from stage 1 are dissolved in 20 ml of tetrahydrofuran and dried over a molecular sieve (3 Angstrom). This is followed by filtering and, under nitrogen, 0.75 g (20 mmoles) of sodium boron hydride are added in portions while stirring for half an hour at room temperature, whereupon 3.8 g (3.4 ml; 27 mmoles) of boron trifluoride etherate are added dropwise at room temperature during one hour. The mixture is then heated for a further hour to 60° C. On cooling to room temperature the mixture is hydrolyzed with 10 ml of a mixture of tetrahydrofuran and water (1:1). The solution is acidified with 7 ml of semi-concentrated hydrochloric acid while cooling on an ice bath. After a reaction time of 30 minutes the solution is adjusted with a solution of caustic soda to a pH value of 7 and extracted three times with diethyl ether, using 30 ml each time. The ether phase is washed with saturated sodium chloride solution until it is neutral, whereupon it is dried over magnesium sulphate. Upon filtering and distilling off the solvent the remaining oil is distilled in a bulb tube. 1.81 g of a gradually solidifying oil are obtained (88% of the theoretical yield). The product has a melting point of 69° to 71° C.

| CHN analysis | % C | % H | % N |
|---|---|---|---|
| $C_9H_{10}F_3NO_3$ computed: | 52.69 | 4.91 | 6.83 |
| obtained: | 53.76 | 5.10 | 7.08 |

Examples 2 to 5: The following compounds are produced analogously to the manner described in Example 1:

2: Stage 1: N-(3-hydroxy-5-methyl)phenyl-2',2',2'-trifluoro acetamide—melting point: 116° to 118° C.
Stage 2: 3-methyl-5-(2',2',2'-trifluoroethyl)aminophenol—melting point: 129° to 131° C.
3: Stage 1: N-(3-hydroxy-2-methyl)phenyl-2',2',2'-trifluoroacetamide—melting point: 114° to 116° C.
Stage 2: 2-methyl-3-(2',2',2'-trifluoroethyl)aminophenol—melting point: 119° to 121° C. 4: Stage 1: N-(3-hydroxy-4-methoxy)phenyl-2',2',2'-trifluoroacetamide—melting point: 140° to 142° C.
Stage 2: 2-methoxy-5-(2',2',2'-trifluoroethyl)aminophenol—melting point: 70° to 71° C.
5: Stage 1: N-(5-hydroxy-2-methyl)phenyl-2',2',2'-trifluoroacetamide—melting point 104° to 106° C.
Stage 2: 4-methyl-3-(2',2',2'-trifluoroethyl)aminophenol—melting point: 64° to 66° C.

Example 6: Production of 2-chloro-5-(2',2',2'-trifluoroethyl) aminophenol

Stage 1: N-(4-chloro-3-hydroxy)phenyl-2',2',2'-trifluoroacetamide

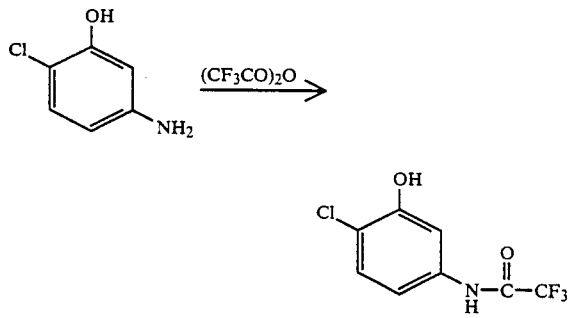

6.0 g (42 mmoles) of 5-amino-2-chloro phenol are dissolved in 75 ml of diethyl ether and, at room temperature, the solution is mixed dropwise with 10.2 ml (15.4 g, 73 mmoles) of trifluoro-acetic acid anhydride. When the exothermic reaction is completed the diethyl ether is distilled off. The crude product obtained (15.5 g) is recrystallized from 20 ml of an ethanol-water mixture (2:1). 3.0 g (91% of the theoretical yield) of a white powder having a melting point of 145° to 147° C. are obtained.

| CHN analysis: | % C | % H | % N |
|---|---|---|---|
| $C_8H_5ClF_3NO_2$ computed: | 40.11 | 2.11 | 5.85 |
| obtained: | 40.10 | 1.92 | 5.85 |

Stage 2: 2-chloro-5-(2',2',2'-trifluoroethyl)aminophenol

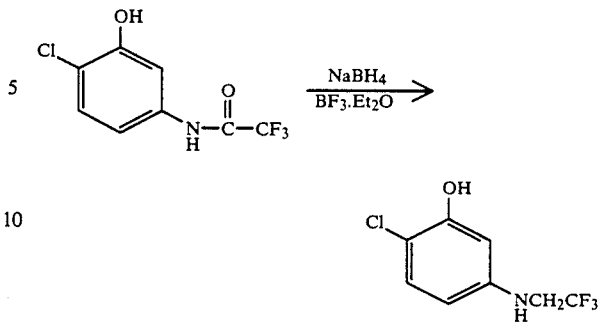

2.0 g (8.3 mmoles) of product from Stage b 1 are dissolved in 14 ml of tetrahydrofuran and dried over a molecular sieve (3 Angstrom). This is followed by filtering, whereupon 0.691 g (16 mmoles) of sodium boron hydride is added in portions under nitrogen, stirring for half an hour at room temperature. Next, at room temperature, 3.53 g (12.34 ml, 25 mmoles) of boron fluoride etherate are added dropwise within one hour. The mixture is then heated for a further hour to 60° C. Upon cooling the mixture, it is hydrolyzed with 6.8 ml of a tetrahydrofuran-water mixture (1:1). The solution is acidified with 4 ml of a semi-concentrated hydrochloric acid while cooling in an ice bath. After a reaction time of 30 minutes the solution is adjusted to a pH value of 7, using a 30% caustic soda solution, and extracted with diethyl ether three times, using 30 ml each time. The ether phase is washed with a saturated sodium chloride solution until neutral and dried over magnesium sulphate. Upon filtering and distilling off the solvent the remaining oil is distilled in a bulb tube (boiling point 130° C/4Pa). 1.34 g (72% of the theoretical yield) of a solidifying oil are obtained. The product has a melting point of 66° to 67.5° C.

| CHN analysis | % C | % H | % N |
|---|---|---|---|
| $C_8H_7ClF_3NO$ computed: | 42.59 | 3.13 | 6.21 |
| obtained: | 42.71 | 3.36 | 6.22 |

EXAMPLES OF HAIR DYES:

Example 7: Hair dye in the form of a cream

| | |
|---|---|
| 1.0 g | of 2-methyl-5-(2',2',2'-trifluoroethyl |
| 0.3 g | of 2-(2',5'-diaminophenyl)ethanol sulphate |
| 1.1 g | of anhydrous sodium sulphite |
| 3.5 g | of lauryl alcohol-diglycol ether sulphate, sodium salt (28 percent aqueous solution) |
| 15.0 g | of cetyl alcohol |
| 4.0 g | of ammonia, 25 percent aqueous solution |
| 75.1 g | of fully desalted water |
| 100.0 g | |

Immediately prior to the application of 50 g of the above hair dye are mixed with 50 g of a 6 percent hydrogen peroxide solution and the mixture is applied to bleached hair. After a reacton time of 30 minutes at 40° C. the hair is rinsed, washed with a shampoo and dried. The hair has assumed a red-violet color.

Example 8: Hair dye solution 0.63 g of 2-chloro-5-(2',2',2'-trifluoroethyl

```
                              aminophenol
       0.61 g    of 2,5-diamino-toluene sulphate
      10.00 g    of lauryl alcohol-diglycol ether sulphate, sodium salt
                 (28 percent aqueous solution)
      10.0 g     of Isopropanol
       0.30 g    of ascorbic acid
      10.00 g    of ammonia, 25 percent aqueous solution
      68.46 g    of fully desalted water
     100.0 g
```

Immediately prior to the use of the above hair dye, 50 g thereof are mixed with 50 g of a 6 percent hydrogen peroxide solution and the mixture is applied to bleached hair. After a reaction time of 30 minutes at 40° C. the hair is rinsed, washed with a shampoo and dried. The hair has been dyed a deep blue black.

Example 9: Hair dye gel

```
       2.5 g   of 2-chloro-5-(2',2',2'-trifluoroethyl)aminophenol
       1.2 g   of 4-aminophenol
       0.3 g   of ascorbic acid
      15.0 g   of oleic acid
       7.0 g   of Isopropanol
       9.0 g   of ammonia, 25% aqueous solution
      65.0 g   of fully desalted water
     100.0 g
```

50 g of the above hair dye are mixed with 50 g of 6 percent hydrogen peroxide solutio immediately prior to its use and the mixture is applied to bleached hair. After a reaction time of 30 minutes at 40° C. the hair is rinsed, washed with a shampoo and dried. The hair has assumed a red shade.

Example 10: Hair dye in the form of a cream

```
       0.9 g   of 2-chloro-5-(2',2',2'-trifluoroethyl)aminophenol
       2.0 g   of diamino-toluene sulphate
       0.7 g   of 5-(2-hydroxyethyl amino-benzodioxol-(1,3)
       0.3 g   of anhydrous sodium sulphite
       3.5 g   of lauryl alcohol-diglycol ether sulphate, sodium salt
               (28 percent aqueous solution)
      15.0 g   of cetyl alcohol
       4.0 g   of ammonia, 25% aqueous solution
      73.6 g   of fully desalted water
     100.0 g
```

Immediately prior to the use of the above hair dye 50 g thereof are mixed with 50 g of a 6 percent hydrogen peroxide solution and the mixture is applied to bleached hair. After a reaction time of 30 minutes at 40° C. the hair is rinsed, washed with a shampoo and dried. The hair has been dyed black.

Examples 11 to 14: Hair dye soluton

Hair dye solutions are produced as in Example 8 but the coupling substance 2-chloro-5-(2',2',2'-trifluoroethyl)amino-phenol has been replaced by one of the following coupling substances according to the present invention. With the hair dye solutions thus obtained a hair treatment like that described in Example 8 is carried out:

11: 3-methyl-5-(2',2',2'-trifluoroethyl)aminophenol. After the hair treatment the hair has been dyed red-brown.

12: 4-methyl-3-(2',2',2'-trifluoroethyl)aminophenol. After the hair treatment the hair has been dyed red-gray.

13: 2-methyl-3-(2',2',2'-trifluoroethyl)aminophenol. After the hair treatment the hair has been dyed cardinal red.

14: 2-methyl-5-(2',2',2'-trifluoroethyl)aminopheno. After the treatment the hair has been dyed red-violet.

Example 15: Hair dye solution

```
       0.63 g   of 2-chloro-5-(2',2',2'-trifluoroethyl)aminophenol
       0.64 g   of tetraamino-pyrimidine-sulphate monohydrate
      10.00 g   of lauryl alcohol diglycol ether sulphate, sodium salt
                (28 percent aqueous solution)
      10.00 g   of Isopropanol
       0.30 g   of ascorbic acid
      10.00 g   of ammonia, 25% aqueous solution
      68.43 g   of fully desalted water
     100.00 g
```

Immediately prior to the use of the above hair dye 50 g thereof are mixed with 50 g of a 6 percent hydrogen peroxide solution and the mixture is applied to bleached hair. After a reaction time of 30 minutes at 40° C. the hair is rinsed, washed with a shampoo and dried. The hair has been dyed steel-blue. Unless otherwise stated the data in percent relate to percent by weight.

I claim:

1. A composition of the oxidative dyeing of hair based on a combination of a coupling substance and a developing substance, which comprises:

(a) 0.01 to 4% by weight of a compound of the Formula (I)

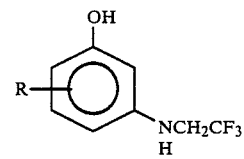

wherein
R is $C_1$ to $C_4$ alkyl, a mono- or polyhydroxy-alkyl containing 1 to 4 carbon atoms and up to 3 hydroxy groups, $C_1$ to $C_4$ alkoxy, a mono- or polyhydroxy-alkoxy containing 1 to 4 carbon atoms and up to 3 hydroxy groups, or a halogen atom, or a physiologically acceptable salt thereof as coupling substance; and (b) a developer substance conventionally used in the preparation of hair dyes, wherein the amount of the coupler substance and the developer substance makes up 0.1 to 6.0% by weight of the composition; together with a physiologically acceptable carrier or diluent.

2. The composition defined in claim 1 wherein the radical R is in the para position relative to the (2',2',2'-trifluoroethyl)amino radical.

3. The composition defined in claim 1 in which the halogen is chlorine.

4. The composition defined in claim 1 in which the physiologically acceptable salt is selected from the choride, the sulfate, the phosphate, the acetate, the proprionate, the lactate and the citrate.

5. The composition defined in claim 1 in which the compound of the Formula (I) is selected from the group consisting of 2-methyl-3-(2',2',2'-trifluoroethyl)aminophenol, 2-methyl-5-(2',2',2'-trifluoroethyl)aminophenol, 2-chloro-5-(2',2',2'-trifluoroethyl)aminophenol, 2- methoxy-5-(2',2',2'-trifluoroethyl)aminophenol and 3-methyl-5-(2',2',2'-trifluoroethyl)aminophenol.

6. The composition defined in claim 1 in which the compound of the Formula (I) is 4-methyl-3-(2',2',2'-trifluoroethyl)aminophenol.

7. The composition defined in claim 1 which contains the coupling substance of the Formula (I) in an amount of 0.02 to 2.0% by weight.

8. The composition defined in claim 1 which contains at least one of the following developer substances: 1,4-diamino-benzene, 2,5-diamino-toluene, 2,5-diamino-anisole, 4-aminophenol, 2,5-diaminobenzyl alcohol, 2-(2',5'-diamino)-phenyl-ethanol, 3-methyl-4-aminophenol, or tetraamino pyrimidine.

9. The composition defined in claim 1 which contains at least one of the following additional coupler substances selected from the group consisting of resorcinol, 4-chlororesorcinol, 4,6-dichlororesorcinol, 2-methyl-resorcinol, 2-amino-4-(2'-hydroxyethyl)amino-anisole, 1,5-dihydroxy-tetralin, 3-amino-2-methyl-phenol, 2,4-diamino-anisole, 2,4-diamino-benzyl alcohol, 5-amino-2-methyl-phenol, 2,4-diamino-phenetole, 1,3-diamino-benzene, 1-naphthol, 4-hydroxy-indole, 5-hydroxy-(1,3)-benzodioxole, 5-amino-(1,3)-benzodioxole, 5-(2'-hydroxyethyl)amino-(1,3)-benzodioxole, 2,4-dihydroxy-anisole, and 2,4-dihydroxy-phenoxy ethanol.

10. The composition defined in claim 1 wherein the total amount of the combination of developer substance and coupler substance contained therein is 0.5 to 3.0% by weight.

11. The composition defined in claim 1 which contains at least one direct dye selected from the group consisting of Diamond Fuchsine (C.I. 42 510), Leather Ruby HF (C.I. 42 520), 2-amino-4,6-dinitro phenol, 3-(2'-hydroxyethyl)-amino-2-nitro-anisole, 2-amino-4-nitro-phenol, Acid Brown 4 (C.I. 14 805), Disperse Blue (C.I. 64 500), Disperse Red 15 (C.I. 60 710), Acid Blue 135 (C.I. 13 385), Disperse Violet 4 (C.I. 61 105), Disperse Violet 1 (C.I. 61 100), 1,4,5,8-tetraamino-anthraquinone and diamino-anthraquinone.

12. The composition defined in claim 1 which contains 2-amino-5-methyl-phenol, 2-amino-6-methyl-phenol, or 2-amino-5-ethoxy-phenol as a self-coupling color prestage.

13. A process for the oxidative dyeing of hair which comprises the steps of:
(a) oxidizing with an oxidizing agent a composition of the oxidative dyeing of hair based on a combination of a coupling substance and a developing substance, which composition comprises:
(i) 0.01 to 4% by weight of a compound of the formula (I)

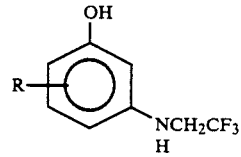

wherein R is $C_1$ to $C_4$ alkyl, a mono- or polyhydroxyalkyl containing 1 to 4 carbon atoms and up to 3 hydroxy groups, $C_1$ to $C_4$ alkoxy, a mono- or polyhydroxy-alkoxy containing 1 to 4 carbon atoms and up to 3 hydroxy groups, or a halogen atom, or a physiologically acceptable salt thereof as coupling substance; and
(ii) a developer substance conventionally used in the preparation of a hair dye, wherein the amount of the coupler substance and the amount of the developer substance makes up 0.1 to 6.0% by weight of the composition; and
(iii) a physiologically acceptable carrier or diluent;
(b) applying the composition oxidized during step (a) to hair in an amount effective to dye the hair;
(c) allowing the composition to act on the hair for 10 to 45 minutes at 15° to 50° C.; and
(d) rinsing the hair with water, and drying the hair.

14. The process for oxidative dyeing of hair defined in claim 13 wherein according to step (a) the oxidizing agent is a 6% aqueous solution of hydrogen peroxide.

* * * * *